United States Patent
Talbot et al.

(10) Patent No.: US 11,723,720 B2
(45) Date of Patent: Aug. 15, 2023

(54) ENDOSCOPIC LASER SYSTEM WITH LASER INTERLOCK

(71) Applicant: GYRUS ACMI, INC., Southborough, MA (US)

(72) Inventors: Brian M. Talbot, Southborough, MA (US); Sergey A. Bukesov, Acton, MA (US); Kurt G. Shelton, Bedford, MA (US); Rachel D. Schnakenberg, Minneapolis, MN (US); Maria Rao, Worcester, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 278 days.

(21) Appl. No.: 16/947,487

(22) Filed: Aug. 4, 2020

(65) Prior Publication Data
US 2021/0038309 A1 Feb. 11, 2021

Related U.S. Application Data

(60) Provisional application No. 63/027,079, filed on May 19, 2020, provisional application No. 62/893,913,
(Continued)

(51) Int. Cl.
*A61B 18/24* (2006.01)
*A61B 1/018* (2006.01)
(Continued)

(52) U.S. Cl.
CPC .......... *A61B 18/24* (2013.01); *A61B 1/00009* (2013.01); *A61B 1/00097* (2022.02);
(Continued)

(58) Field of Classification Search
CPC . A61B 18/24; A61B 1/00097; A61B 1/00009; A61B 1/018; A61B 1/0676;
(Continued)

(56) References Cited

U.S. PATENT DOCUMENTS 3,608,547 A * 9/1971 Sato ................... A61B 1/00165
600/117
3,744,906 A * 7/1973 Sato ................... A61B 1/00165
356/3
(Continued)

FOREIGN PATENT DOCUMENTS

CN 114401661 A 4/2022
DE 112020003713 T5 4/2022
(Continued)

OTHER PUBLICATIONS

"Indian Application Serial No. 202247004789, First Examination Report dated Jun. 22, 2022", 7 pgs.
(Continued)

*Primary Examiner* — Aaron F Roane
(74) *Attorney, Agent, or Firm* — Schwegman Lundberg & Woessner, P.A.

(57) ABSTRACT

Systems, devices, and methods for determining advancement of a surgical laser fiber in an endoscope and providing interlocking feedback for the surgical laser are disclosed. An exemplary method includes directing light from a distal end of an endoscope to a target, optically detecting an amount of the light reflected from the target, transmitting the optically detected amount of light through a laser fiber extending through a working channel of the endoscope, determining, based on the optically detected amount of light, a position of a distal end of the laser fiber relative to the distal end of the endoscope, and generating a control signal to the surgical laser system to adjust laser emission through the laser fiber.

23 Claims, 9 Drawing Sheets

Related U.S. Application Data filed on Aug. 30, 2019, provisional application No. 62/882,837, filed on Aug. 5, 2019.

(51) Int. Cl.
  *A61B 1/06*    (2006.01)
  *A61B 1/00*    (2006.01)
  *A61B 5/00*    (2006.01)
  *A61B 17/00*   (2006.01)
  *A61B 18/00*   (2006.01)

(52) U.S. Cl.
  CPC ............ *A61B 1/018* (2013.01); *A61B 1/0676* (2013.01); *A61B 5/0075* (2013.01); *A61B 2017/00061* (2013.01); *A61B 2018/00642* (2013.01); *A61B 2018/00982* (2013.01)

(58) Field of Classification Search
  CPC ........ A61B 5/0075; A61B 2017/00061; A61B 2018/00642; A61B 2018/00982
  USPC .......................................................... 606/15
  See application file for complete search history.

(56) References Cited

U.S. PATENT DOCUMENTS

| | | | |
|---|---|---|---|
| 6,554,824 | B2 | 4/2003 | Davenport et al. |
| 9,017,316 | B2 | 4/2015 | Khatchaturov et al. |
| 9,445,871 | B2 | 9/2016 | Kang et al. |
| 9,486,286 | B2 | 11/2016 | Hodel et al. |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 2013/0072753 | A1* | 3/2013 | Zappia ................. A61B 1/0008 600/104 |
| 2015/0224249 | A1 | 8/2015 | Ciulla et al. |
| 2015/0230864 | A1 | 8/2015 | Xuan et al. |
| 2015/0272674 | A1 | 10/2015 | Xuan et al. |
| 2016/0081749 | A1* | 3/2016 | Zhang ................... A61B 18/22 606/15 |
| 2016/0166319 | A1 | 6/2016 | Yu et al. |
| 2018/0092693 | A1 | 4/2018 | Falkenstein et al. |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0246908 | A1 | 8/2019 | Pyun et al. |
| 2019/0298449 | A1 | 10/2019 | Khachaturov et al. |
| 2019/0393669 | A1 | 12/2019 | Yu et al. |

FOREIGN PATENT DOCUMENTS

| | | |
|---|---|---|
| EP | 3510962 | 7/2019 |
| EP | 3512448 | 7/2019 |
| EP | 3522811 | 8/2019 |
| WO | 1990014797 | 12/1990 |
| WO | 2013043344 | 3/2013 |
| WO | 2014074678 | 5/2014 |
| WO | 2020033121 | 2/2020 |
| WO | WO-2021026157 A1 | 2/2021 |

OTHER PUBLICATIONS

"International Application Serial No. PCT/US2020/044891, International Preliminary Report on Patentability dated Feb. 17, 2022", 9 pgs.

"International Application Serial No. PCT US2020 044891, International Search Report dated Oct. 16, 2020", 5 pgs.

"International Application Serial No. PCT US2020 044891, Written Opinion dated Oct. 16, 2020", 7 pgs.

Bosschaart, Nienke, et al., "A literature review and novel theoretical approach on the optical properties of whole blood", Lasers Med Sci, (2014), 453-479.

Jacques, Steven, "Optical Absorption of Carbonized Tissue", [Online], Retrieved from the Internet: <URL: https://omlc.org/spectra/carbon/>, (2018), 3 pgs.

Vinnichenko, Victoriya, et al., "Comparison of a novel high-power blue diode laser ($\lambda$ A = 442 nm) with Ho:YAG ($\lambda$ = 2100 nm), Tm fiber ($\lambda$ = 1940 nm), and KTP ($\lambda$ = 532 nm) lasers for soft tissue ablation", Proc. SPIE 10468, Therapeutics and Diagnostics in Urology, [Online], Retrieved from the Internet: <URL: : https://www.researchgate.net/publlcation/323002187>, (Feb. 2018), 8 pgs.

\* cited by examiner

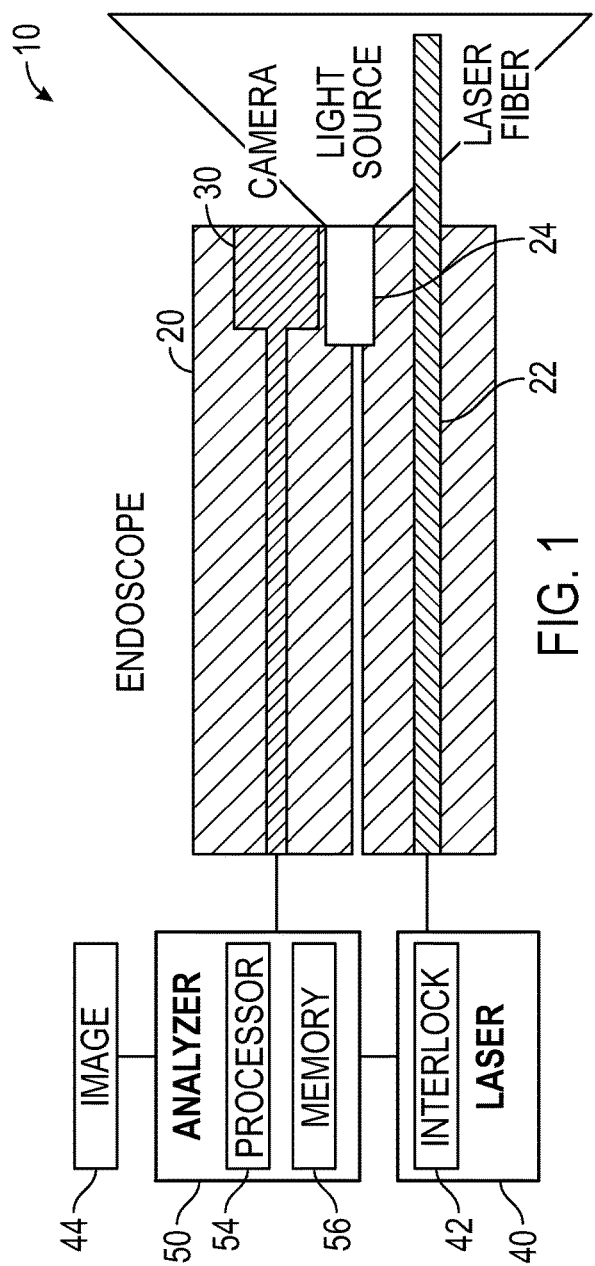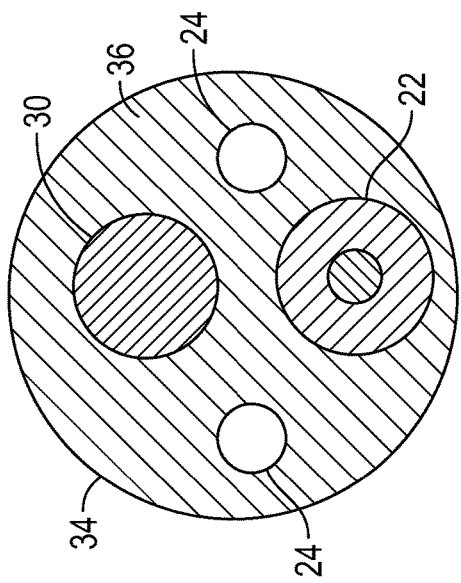

ENDOSCOPIC LASER SYSTEM WITH LASER INTERLOCK

CLAIM OF PRIORITY

This application claims the benefit of priority under 35 U.S.C. § 119(e) of U.S. Provisional Patent Application Ser. No. 62/882,837, filed on Aug. 5, 2019, U.S. Provisional Patent Application Ser. No. 62/893,913, filed on Aug. 30, 2019, and U.S. Provisional Patent Application Ser. No. 63/027,079, filed on May 19, 2020, which are herein incorporated by reference in their entireties.

TECHNICAL FIELD

This document relates generally to surgical lasers, and more particularly to systems and methods of determining advancement of a surgical laser fiber in an endoscope and providing interlocking feedback for the surgical laser.

BACKGROUND

Laser or plasma systems have been used for delivering surgical laser energy to various target treatment areas such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments.

Endoscopes are typically used to provide access to an internal location of a subject such that a physician is provided with visual access. An endoscope is normally inserted into a patient's body, delivers light to a target (e.g., a target anatomy or object) being examined, and collects light reflected from the object. The reflected light carries information about the object being examined and can be used to create an image of the object. Some endoscopes include a working channel through which the operator can perform suction or pass instruments such as brushes, biopsy needles or forceps, or perform minimally invasive surgery to remove unwanted tissue or foreign objects from the body of the patient.

SUMMARY

In accordance with one aspect of the invention, a method of feedback control of a surgical laser system comprises: directing light from a distal end of an endoscope to a target; optically detecting an amount of the light reflected from the target; transmitting the optically detected amount of light through a laser fiber extending through a working channel of the endoscope; determining, based on the optically detected amount of light, a position of a distal end of the laser fiber relative to the distal end of the endoscope; and generating a control signal to the surgical laser system to adjust laser emission through the laser fiber.

In accordance with another aspect of the invention, a laser feedback control system comprises: an endoscope including an optical detector configured to detect an amount of light reflected from a target in response to illumination of the target from a distal end of the endoscope; a laser fiber extending through a working channel of the endoscope, the laser fiber configured to transmit the detected amount of light reflected from the target; and a controller configured to: determine, based on the optically detected amount of light, a position of a distal end of the laser fiber relative to the distal end of the endoscope; and generate a control signal to a surgical laser system to adjust laser emission through the laser fiber.

In accordance with another aspect of the invention, an apparatus comprises: at least one processor; and at least one non-transitory memory including computer program code, the at least one non-transitory memory and the computer program code configured to, with the at least one processor, cause the apparatus at least to perform: directing light from a distal end of an endoscope to a target; optically detecting an amount of the directed light reflected from the target; transmitting the optically detected amount of light through a laser fiber extending through a working channel of the endoscope; determining, based on the optically detected amount of light, a position of a distal end of the laser fiber relative to the distal end of the endoscope; and generating a control signal to a surgical laser system to adjust laser emission through the laser fiber.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 1 is a schematic side view representation of a system employing an endoscope and a surgical laser.

FIG. 2 is a schematic end view representation of the system of FIG. 1.

DETAILED DESCRIPTION

Figure 3:
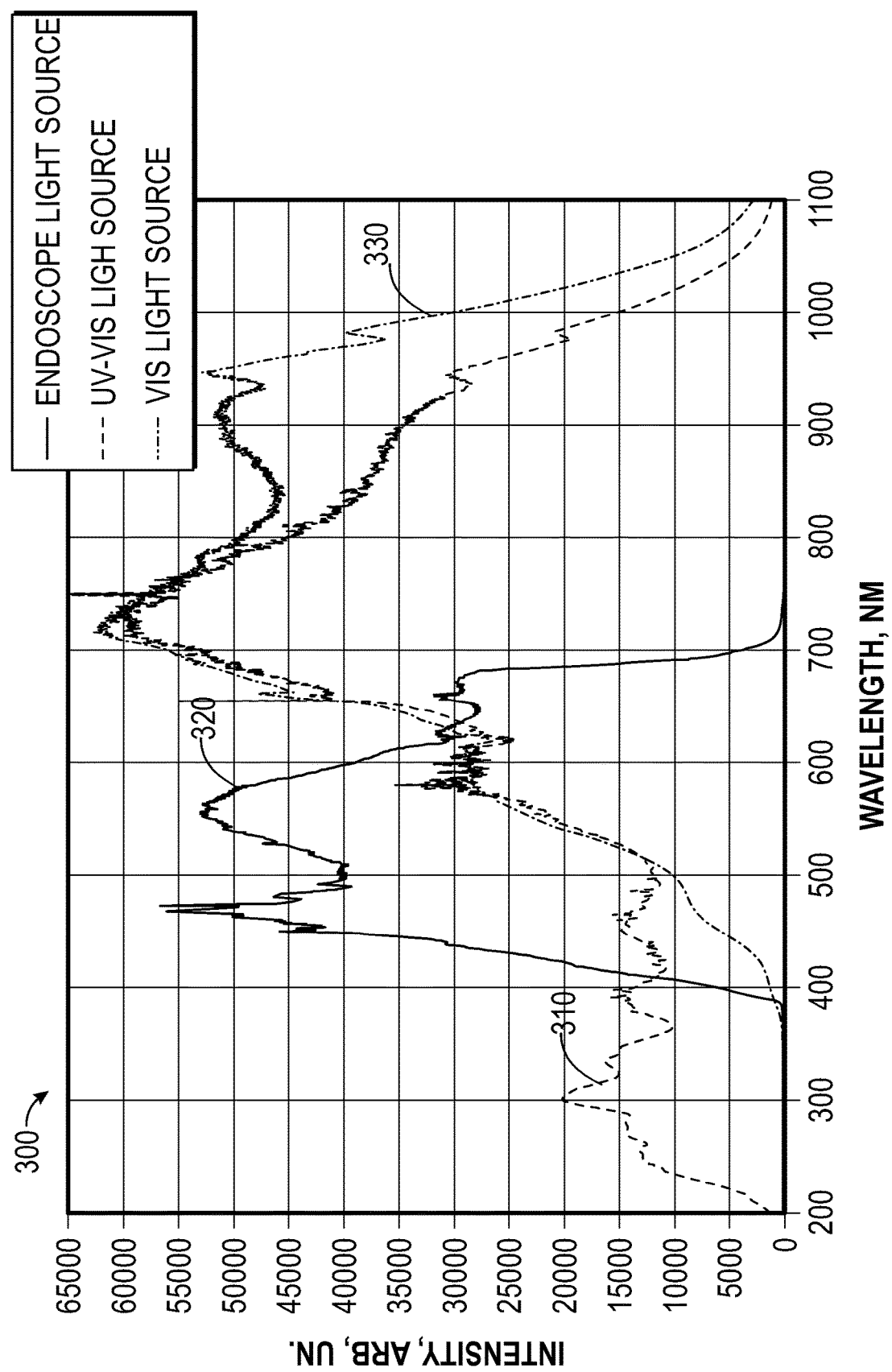
FIG. 3 is a graphical representation of spectra of light sources used with various endoscopes.

Damage to endoscopes during surgical procedures can result in costly repairs to the endoscope, delays in surgical procedures, and/or damage to other equipment. Currently in laser endoscopic procedures there is no way of protecting the inner workings of the endoscope against accidental laser emission while the laser fiber is inside the working channel of a scope. Accidental laser emission may result in back-reflectance that can damage the laser system or in physical damage to the endoscope, thereby impeding the instrument's ability to be navigated by a user or interfering with the visualization of patient target areas.

The ability to detect when a laser fiber has advanced outside of an endoscope may help to prevent equipment damage and patient surgical delays. This detection may be accomplished with equipment used to perform an endoscopic procedure configured as described herein.

The embodiments described herein address the problem of the accidental firing of a surgical laser system inside an endoscope in that methods are employed to identify when a surgical laser fiber transitions from being inside the working channel of an endoscope to being outside of the endoscope. The methods use the light source(s) associated with the endoscopic instrument and the surgical laser fiber used to treat the patient. An optical feedback system is incorporated into the surgical laser system which would restrict laser emission through the laser fiber while the laser fiber is still inside the endoscope. This interlocking feature of the system can be functional on a wide variety of endoscopes and laser fiber sizes.

The embodiments described herein also protect against fibers that break within the endoscope. Even if the surgical laser fiber has exited the endoscope but the fiber breaks within the endoscope, the system is able to detect the break as the new "tip" of the surgical laser fiber and recognize that the new tip (which is now the end) is still inside the endoscope, preventing further laser emission inside of the endoscope.

The methods may be carried out by measuring optically detected reflectance back through the surgical laser fiber. The reflected light comes from the light source used in the endoscopic procedure. The light source may be selected from a wide array of light sources. A lack of optical detection of a reflected signal back through the surgical laser fiber (or optical detection less than a predetermined value) causes a determination that the surgical laser fiber is within the working channel of the endoscope. Optical detection of a reflected signal greater than a predetermined value back through the surgical laser fiber causes a determination that the surgical laser fiber has been advanced enough through the working channel to have exited the endoscope. In this manner, the position of the distal end of the surgical laser fiber can be ascertained before emitting laser energy.

Referring to FIG. 1, a system employing an endoscope and a surgical laser for use in surgical endoscopy procedures is shown generally at 10 and is hereinafter referred to as "system 10." System 10 includes an endoscope 20 operably coupled to a laser 40 and to a feedback analyzer 50. The endoscope 20 includes a surgical laser fiber 22, at least one light source 24, and an optical detector 30 (which may include a camera). The surgical laser fiber 22, the light source 24, and the optical detector 30 are located in a sheath 34 (shown in FIG. 2). The laser 40 is operably coupled to the surgical laser fiber 22 and the feedback analyzer 50, both of which may be remote from the endoscope 20. The laser 40 may include a laser interlock 42. The feedback analyzer 50 is operably coupled to the laser interlock 42 and may include a processor 54 and memory 56 having program code associated therewith. In some embodiments, the system 10 may provide input data to another system, such as an image processor 44, whereby a monitor or other type of display displays information to the user, the displayed information being relevant to the emission capabilities of the laser 40.

Referring to FIG. 2, the sheath 34 is tubular and has a generally circular cross-section that defines a working channel 36. The surgical laser fiber 22, the light source 24 (two are shown), and the optical detector 30 are suitably arranged within the working channel 36. Although these components are shown being spaced apart from one another, it should be understood that such components may be suitably tightly packed in the working channel 36 in contact with each other or having minimal space therebetween.

With regard to the laser 40, such a fiber integrated laser system may be used for endoscopic procedures due to its ability to pass laser energy through a flexible endoscope and to effectively treat hard and soft tissue. These laser systems produce a laser output beam in a wide wavelength range from ultraviolet (UV) to infrared (IR) (200 nanometers (nm) to 10000 nm). Some fiber integrated lasers produce an output in a wavelength range that is highly absorbed by soft or hard tissue, for example 1900 nm to 3000 nm for water absorption or 400 nm to 520 nm for oxyhemoglobin and/or deoxyhemoglobin absorption. Table 1 below is a summary of a list of IR lasers that emit in the high water absorption range (1900 nm to 3000 nm).

TABLE 1

Types of IR Lasers

| Laser | Wavelength λ (nm) | Absorption Coefficient $\mu_s$ (cm$^{-1}$) | Optical Penetration Depth δ (μm) |
| --- | --- | --- | --- |
| Thulium fiber laser: | 1908 | 88/150 | 114/67 |
| Thulium fiber laser: | 1940 | 120/135 | 83/75 |
| Thulium: YAG: | 2010 | 62/60 | 161/167 |
| Holmium: YAG: | 2120 | 24/24 | 417/417 |
| Erbium: YAG: | 2940 | 12,000/1,000 | 1/10 |

Some fiber integrated laser systems produce a laser light output in a wavelength range that is minimally absorbed by the target soft or hard tissue. This type of laser provides effective tissue coagulation due to a penetration depth that is similar to the diameter of a small capillary, for example about 5 micrometers (μm) to about 10 μm. Example laser sources for lasers applicable to this embodiment include, but are not limited to, a) UV-VIS emitting InXGa1-XN semiconductor lasers (for example, GaN in which the emission is 515 nm to 520 nm, and InXGa1-XN in which the emission is 370 nm to 493 nm); b) GaXAl1-XAs in which the emission is 750 nm to 850 nm; and c) InXGa1-XAs in which the emission is 904 nm to 1065 nm An endoscopic light source (such as the light source 24) as it would be used for an endoscopic procedure may be used in conjunction with a surgical laser system (such as the laser 40) and the fiber (such as the surgical laser fiber 22) to provide the laser interlock 42 on the system 10. The endoscopic light source may be any light source capable of providing suitable illumination and being compatible with an appropriate endoscope. FIG. 3 shows, at 300, the spectra of three different light sources—UV-VIS light source 310, endoscope light source 320, and VIS light source 330, any of which may be used as the light source 24, which may be used to collect preliminary data with a variety of endoscopes. Such light source 24, typically displayed as white light for the procedure, can span into the UV and IR spectra as well. This expanded range of wavelengths in the light source 24 may be particularly useful for the feedback analyzer 50 of the system 10.

The light sources shown in Table 2 are additional light sources and wavelengths that may be used in the endoscopic light sources to promote accurate reflectance in an optimal range:

TABLE 2

Light sources for spectroscopic system

| Application | Wavelength Range | Type |
|---|---|---|
| Color/VIS/NIR | 360-2500 nm | Tungsten Halogen |
| DUV | 190-400 nm | Deuterium |
| UV | 215-400 nm | Deuterium |
| UV/VIS/NIR reflection/absorption | 215-2500 nm | Deuterium/Halogen |
| UV/VIS/NIR absorption | 200-2500 nm | Deuterium/Halogen |
| UV/VIS | 200-1000 nm | Xenon |
| FTIR | 2000-25000 nm | Silicon Carbide |
| UV/VIS/IR Fluorescence | Multiple narrow emitting | LED, Laser Diode |

Referring back to FIGS. 1 and 2, in one exemplary embodiment of the system 10, light from the light source 24 can be transmitted from the endoscope 20 (or any applicable endoscope) used to treat a patient as long as there is an ability to direct the light from the light source 24 to a target area. The endoscope 20 may be rigid, semi-rigid, or flexible. Endoscopes 20 that may be used with laser surgical procedures include ureteroscopes, cystoscopes, nephroscopes, and resectoscopes. The system 10 as described herein is intended to be used with any combination of endoscope type and flexibility, as well as any other endoscope, not mentioned, that is designed to receive a surgical laser fiber for patient care.

The surgical procedures performed with the system 10 are effectuated via the surgical laser fiber 22. A surgical laser fiber 22 may have a core diameter in a range from about 50 μm to about 1000 μm. A material of which the surgical laser fiber 22 is constructed is compatible with the wavelength used to transmit the laser energy, but should also allow for the transmittance of the wavelength of interest coming from the light source 24 and reflected from the target area.

The optical detector 30 reads the reflected light that travels through the surgical laser fiber 22 to the target area. A light source signal from the light source 24 and reflected from the target area to the optical detector 30 is also collected and delivered, along with the reflected light from the surgical laser fiber 22, to the feedback analyzer 50.

The optical detector 30 may be a dedicated optical detector tuned to the wavelength of interest for the system 10, or it may be an incorporated spectroscopy system in the system 10. Spectroscopy/spectrometry techniques used in physics and chemistry for the identification of various materials through the spectrum reflected, transmitted, emitted, or absorbed by such materials may be employed in the system 10. Optical spectroscopy is a powerful method that is used for easy and rapid analysis of organic and inorganic materials and has the following advantages: a) easy integration with fiber laser delivery system; b) non-destructive methods of material chemical composition analyses; c) allowance for the detection of material compositions in real time; and d) applicability to analyses of different types of materials (for example, hard and soft tissue, stones, and the like). Other advantages may exist.

The following spectroscopic techniques may be used alone or in combination to analyze tissue chemical composition and create the spectroscopic feedback:

UV-VIS reflection spectroscopy: This method gathers information from the light reflected off an object similar to the information yielded from the eye or a color image made by a high resolution camera, but more quantitatively and objectively. The reflection spectroscopy offers information about the material since light reflection and absorption depends on its chemical composition and surface properties. It is also possible to get unique information about both surface and bulk properties of the sample using this technique. The reflection spectroscopy can be a valuable technique to recognize composition of hard or soft tissue.

Fluorescent spectroscopy: This is a type of electromagnetic spectroscopy that analyzes fluorescence from a sample. It involves using a beam of light, usually UV, that excites a material compound and causes it to emit light, typically in visible or IR area. The method is applicable for analysis of some organic components such as hard and soft tissue.

Fourier-Transform Infrared Spectroscopy (FTIR): This is a method used for easy and rapid material analysis. This technique has relatively good spatial resolution and gives information about the chemical composition of the material.

Raman spectroscopy: Raman chemical analysis shows good accuracy in identifying hard and soft tissue components. As a high spatial resolution technique, it is also useful for determining distribution of components within a target.

In some embodiment one or more types of spectroscopy can be used within the endoscope 20 to identify the presence of reflected light. An endoscopic light source signal reflected from the target can be rapidly detected and delivered to the spectrometer though the surgical laser fiber. Alternatively, the detector can be a simple optical module dedicated to the detection of the endoscopic wavelength of interest.

Still referring to FIGS. 1 and 2, the feedback analyzer 50 uses the light delivered back through the surgical laser fiber 22 as feedback to make a determination as to whether the distal end of the surgical laser fiber 22 has advanced beyond the distal end of the working channel 36 of the endoscope 20. In some embodiments, the feedback analyzer 50 may make a determination that the surgical laser fiber 22 is located fully in the working channel 36 and may, for example, indicate such to the user via a red light (or similar signal). Based on the feedback, the feedback analyzer 50 may interface with the laser interlock 42 to prevent the laser 40 from firing, even when in emission mode and the user makes an intentional attempt to fire the laser. The laser interlock 42 would also prevent the unintentional firing of the laser 40. Until the surgical laser fiber 22 has left the endoscope 20 by protruding from the sheath 34, based on the reflectance of the light source 24 delivered back through the surgical laser fiber 22, the laser 40 will remain restricted from firing.

Figure 4:
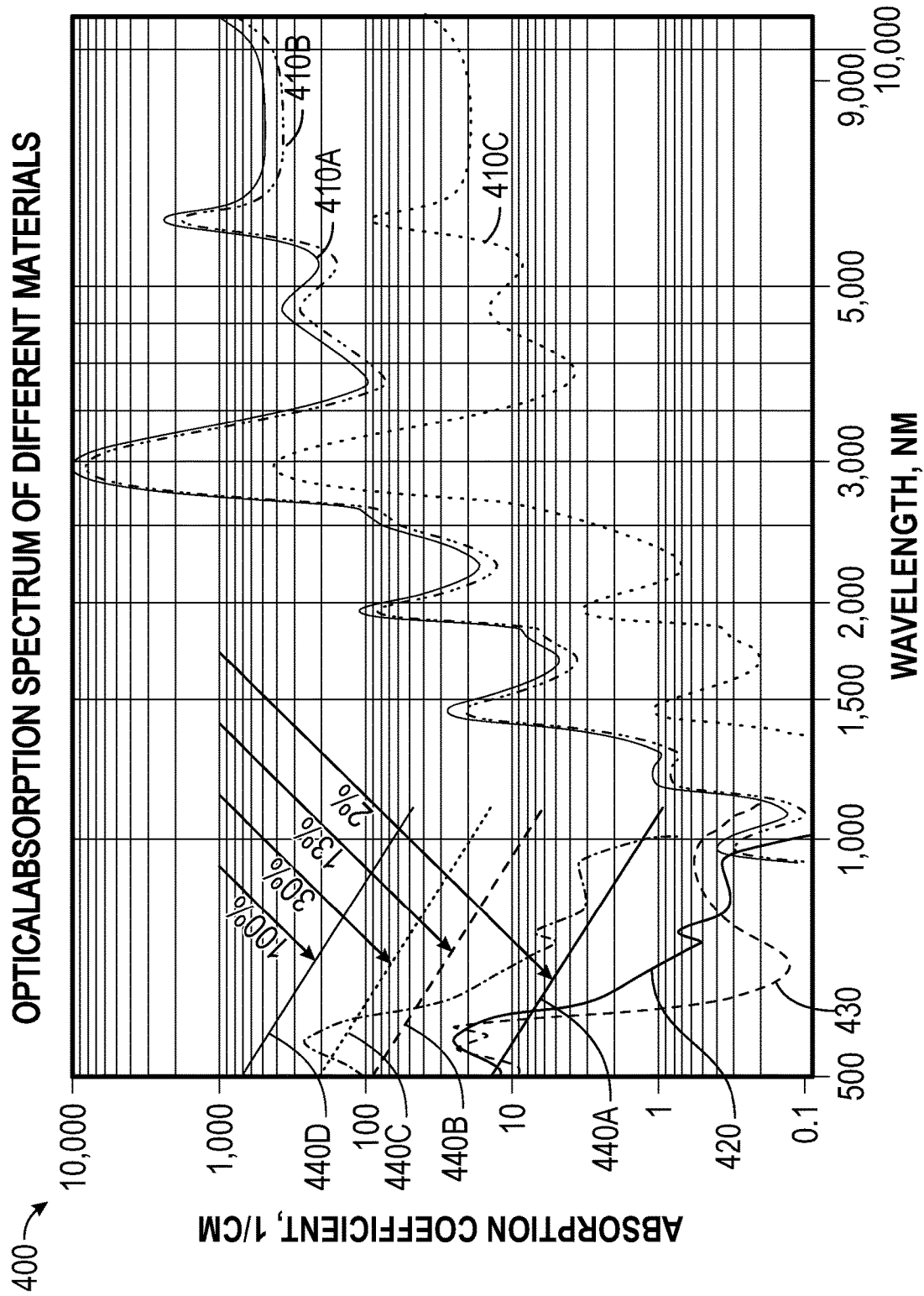
FIG. 4 is a graphical representation of optical absorption spectrums of water, hemoglobin, oxyhemoglobin, and melanin.

A laser emission may be highly absorbed by soft or hard tissue, stone, etc. Referring now to FIG. 4, optical absorption spectra measured in different media across a wavelength range are shown generally at 400. Illustrated therein includes spectra for water 410A-410C (at 75%, 100%, and 4% concentration, respectively), spectra for hemoglobin (Hb) 420, spectra for oxyhemoglobin ($HbO_2$) 430, and spectra for melanin 440A-440D (for volume fractions of melanosomes in 2%, 13%, 30%, and 100%, respectively). The wavelengths for water absorption are in the range of 1900 nm to 3000 nm. The wavelengths for oxyhemoglobin and/or oxyhemoglobin are in the range of 400 nm to 520 nm.

Figure 5:
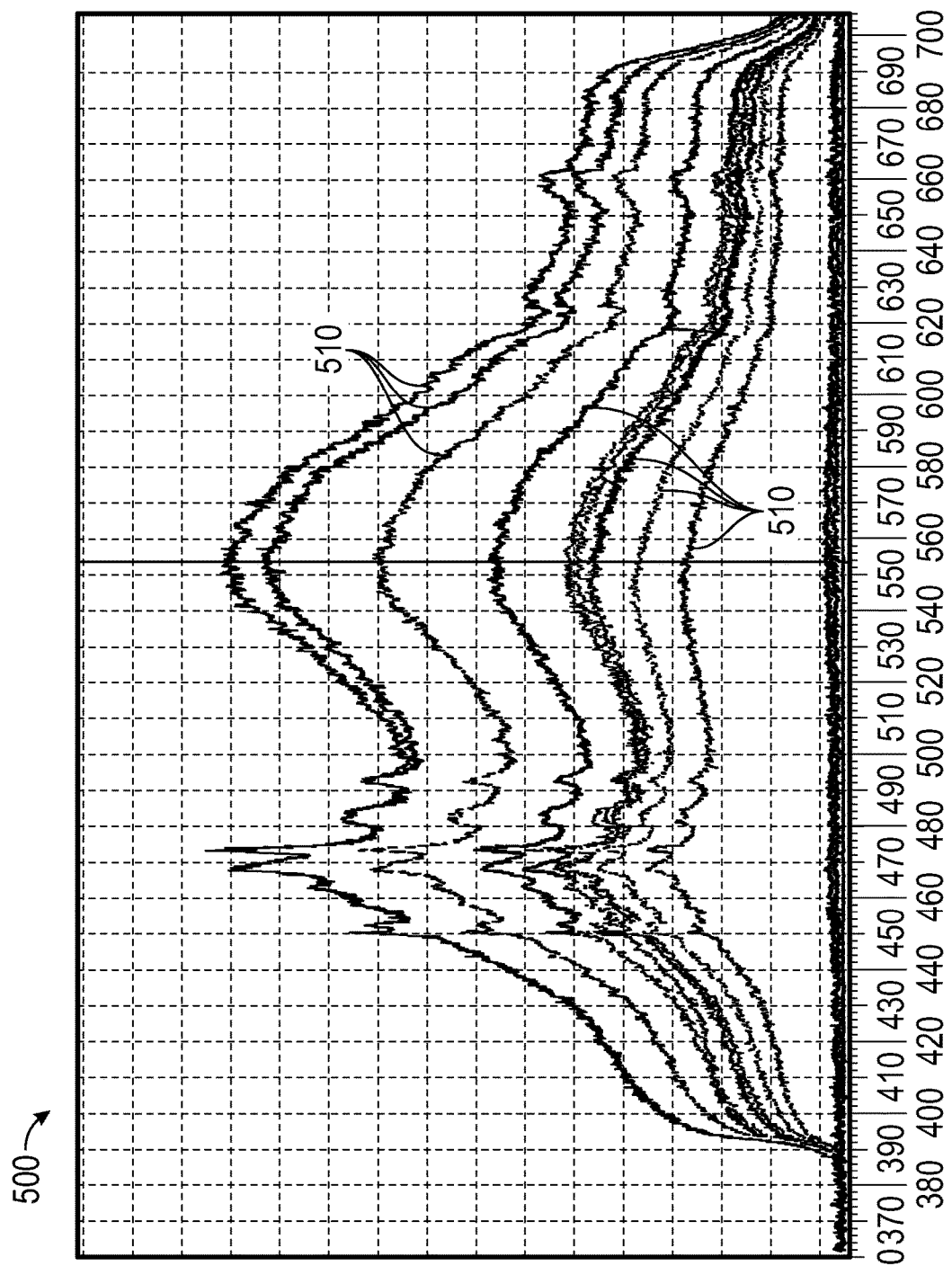
FIG. 5 is a graphical representation of light source spectra detected through a surgical laser fiber at different distances from the tip of the endoscope.
Figure 6:
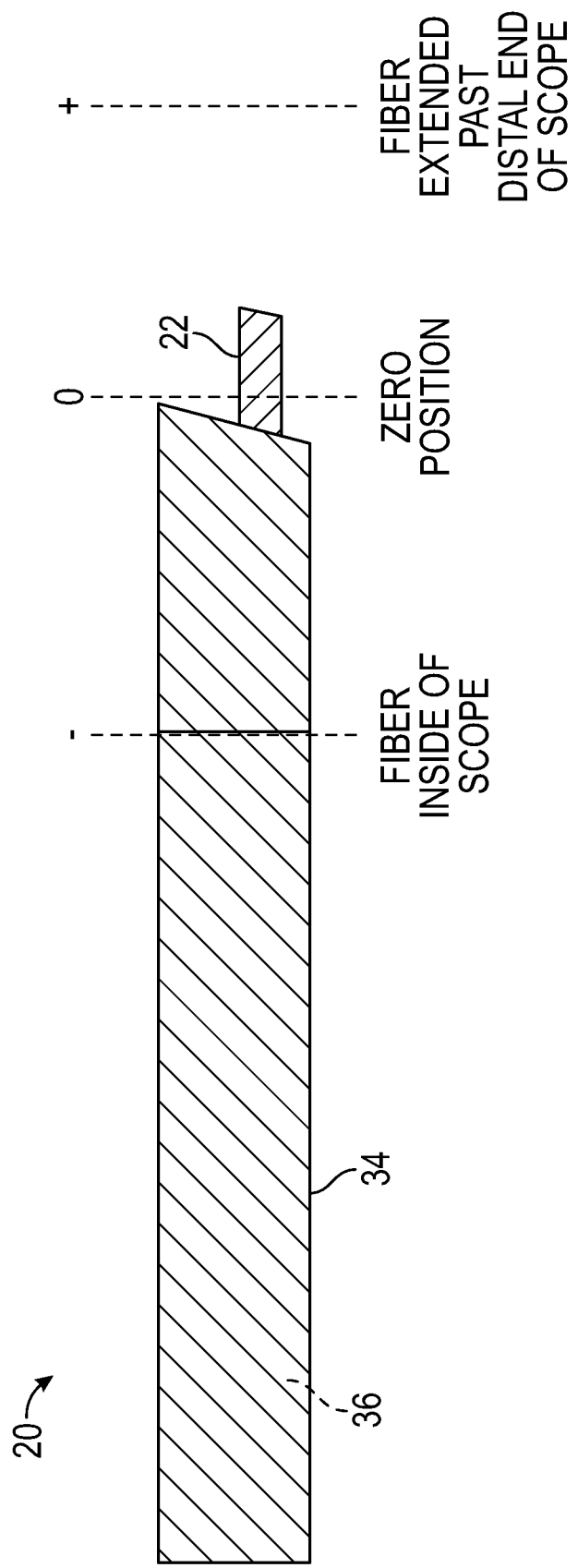
FIG. 6 is a schematic side view representation of a portion of the endoscope of the system of FIG. 1 showing distances of the surgical laser fiber from the tip of the endoscope.

FIGS. 1, 4, 5, and 6 demonstrate how the endoscope 20 may be used in conjunction with the system 10. FIG. 4 shows the absorption of the laser technology in different media. Though many surgical lasers are highly absorbed in water or hemoglobin, inside a scope, there is limited media to absorb the water, which may be a reason for the inside of an endoscope becoming damaged by laser energy. FIG. 1 shows the fundamental setup of the system 10 to detect the reflectance from the light source 24. FIG. 5 shows, at 500, spectroscopic outputs 510 of reflected light from the light source 24 as detected through the surgical laser fiber 22 as the surgical laser fiber 22 progresses (either advances or retracts) through the working channel 36 of the endoscope 20. FIG. 6 shows the basic setup for the surgical laser fiber 22 as it passes through the working channel 36 and leaves a distal end of the endoscope 20.

Figure 7:
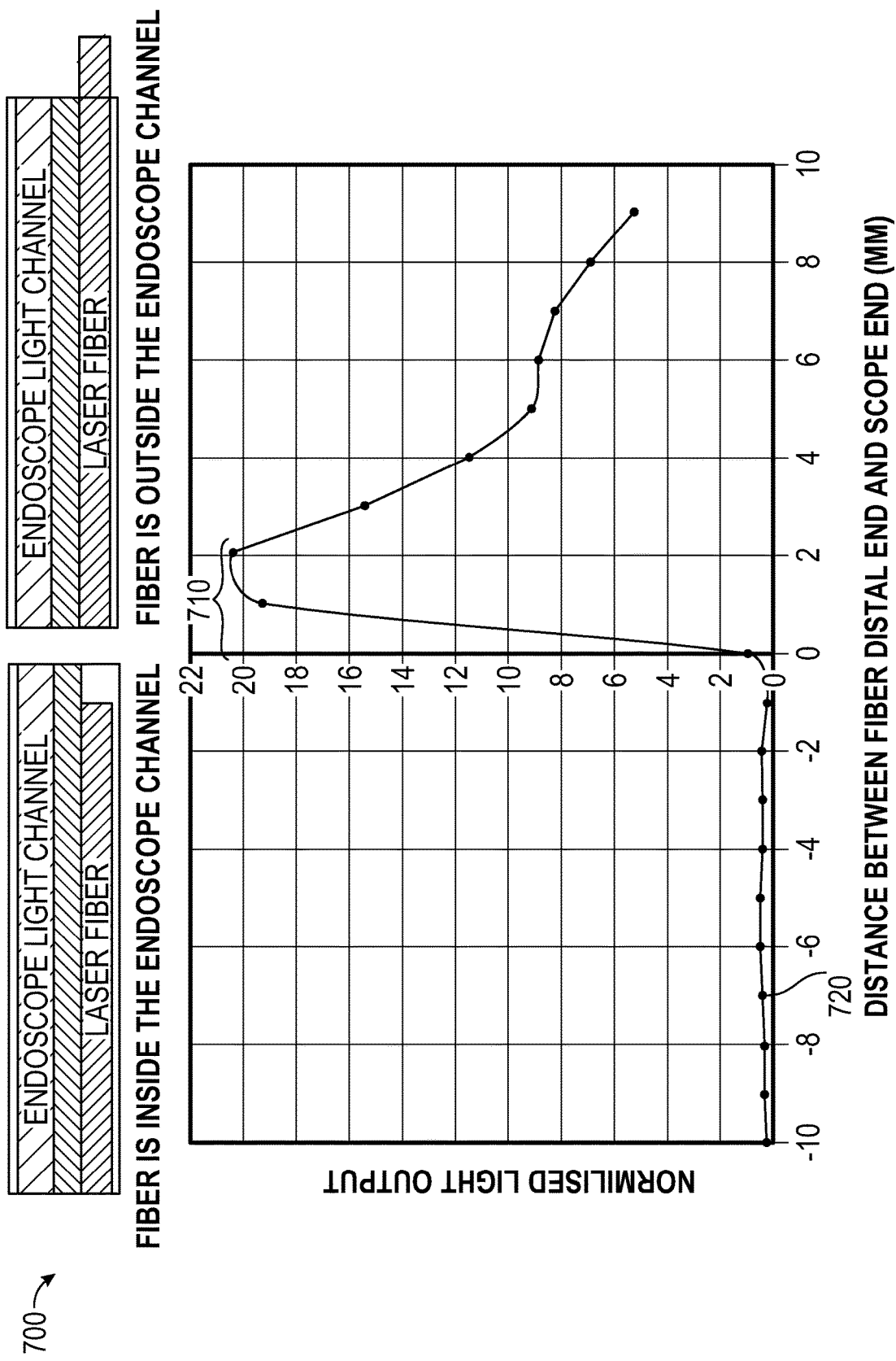
FIG. 7 is a graphical representation of data showing a detected reflectance of a surgical laser fiber of the system of FIG. 1.

Referring now to FIG. 7, feasibility data for identifying when the surgical laser fiber 22 exits the working channel 36 is shown generally at 700. The data was collected by advancing a surgical laser fiber 22 having a 200 μm core into a flexible ureteroscope with a compatible light source 24 acting as the light signal source. This feasibility data 700 shows a significant increase 710 in a detected signal 720 when the surgical laser fiber 22 moves to the end of the working channel 36 and that it is possible to distinguish between the surgical laser fiber 22 being retracted into and advanced beyond the working channel 36. Using this detection technique, data from the optical detector 30 may be processed in the feedback analyzer 50 to prevent accidental laser emission.

Figure 8B:
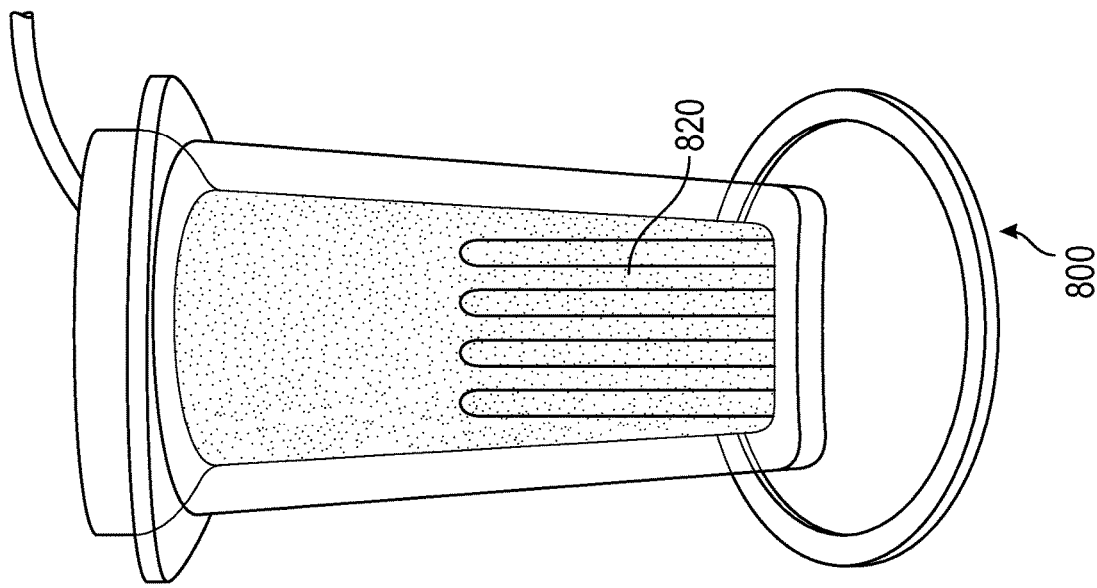
FIGS. 8A and 8B are test setups showing light being deflected into various solutions.
Figure 8A:
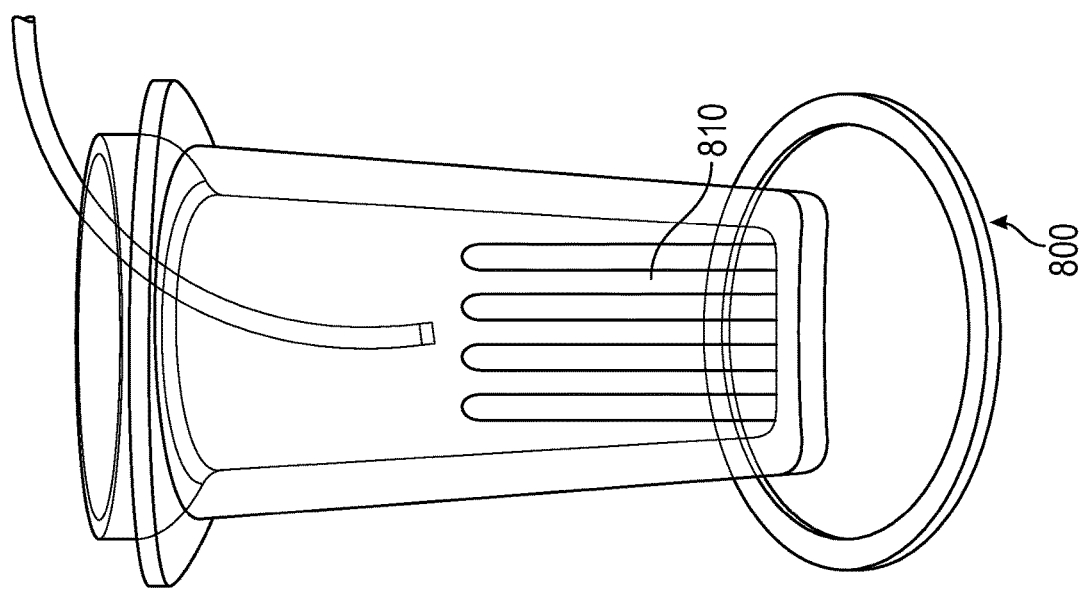

FIGS. 8A and 8B illustrate a simulation setup 800 showing light from the surgical laser fiber 22 is deflected into a container with phosphate buffered saline and calcium oxalate hydrate powder, which simulate compositions that may be experienced during a clinical procedure. FIG. 8A depicts a test setup with light being deflected into a phosphate buffered solution 810 (PBS 810), and FIG. 8B depicts a test setup with light being deflected into PBS with calcium oxalate hydrate 820. The setup in FIG. 8B provides a cloudy, white calcium oxalate hydrate solution 820 (depicted in shades) in contrast to a clear and transparent phosphate buffered solution 810. The calcium oxalate hydrate solution 820 may promote additional reflection and light scattering.

Figure 9:
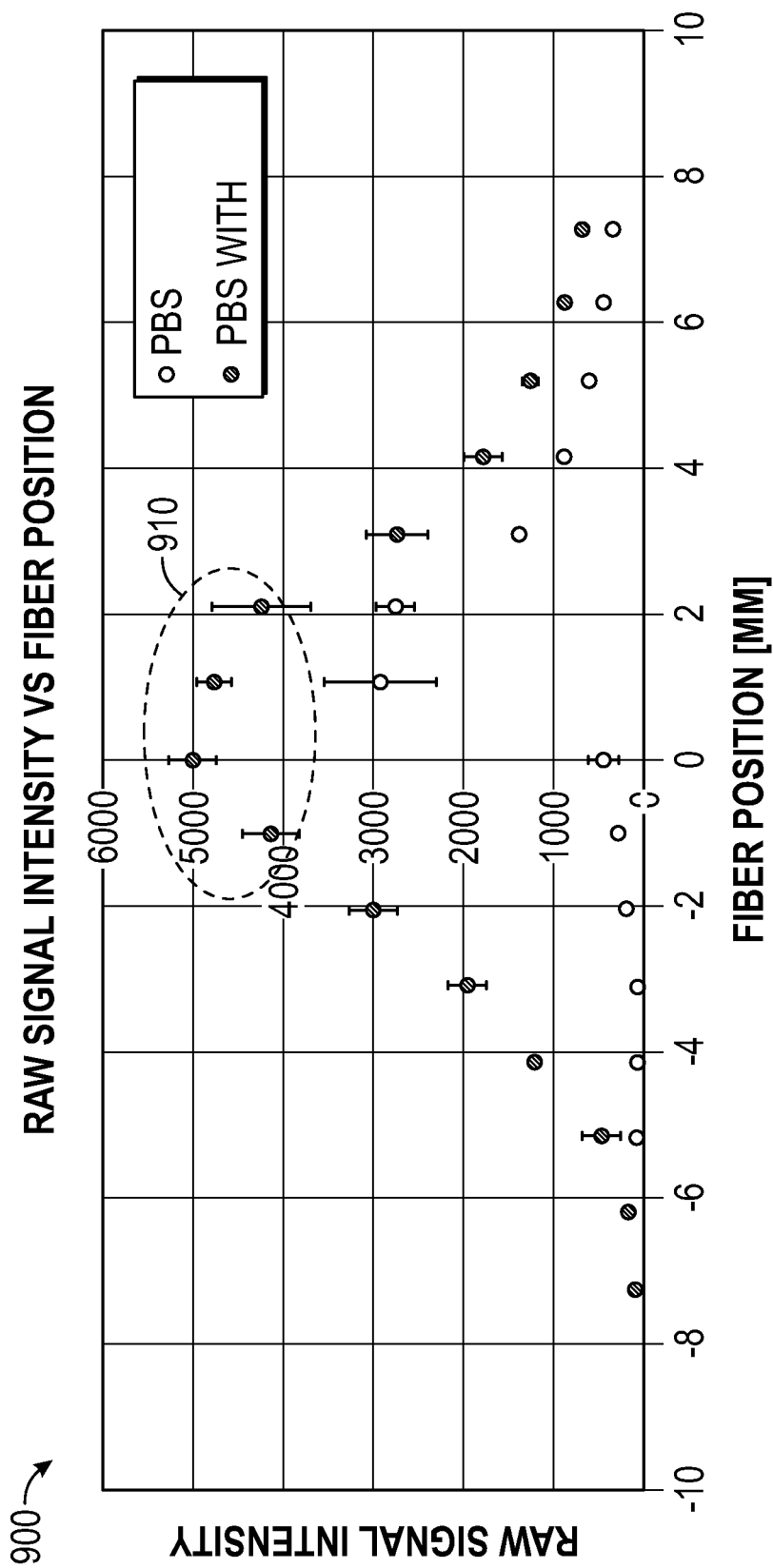
FIG. 9 is a graphical representation of data showing reflectance in a simulation of a potential clinical environment.

Referring to FIG. 9, at 900, data points shown illustrate the reflectance when the light from the endoscope 20 is deflected into the PBS (open circles) and PBS calcium oxalate solutions (PBS with COM, filled circles). At 910, this data shows a higher detection of the source light signal while the surgical laser fiber 22 is in the working channel 36 of the endoscope 20 and that the data trends are the same as when tested in air. Algorithms implemented in the feedback analyzer 50 would be able to account for trends in the data and determine when the surgical laser fiber 22 protrudes from the distal end of the endoscope 20.

Figure 10:
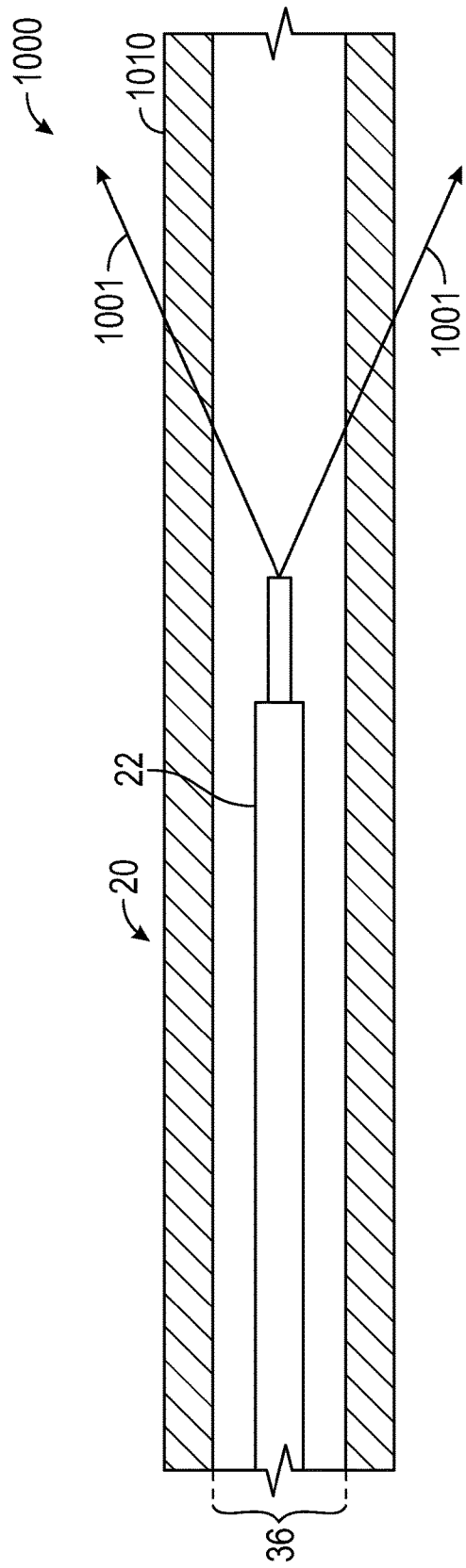
FIG. 10 is a diagram illustrating a transparent liner on the lumen of the working channel of an endoscope.

Damage to endoscope associated with accidental laser firing from within the working channel 36 may be attributed to a transparent working channel liner of the endoscope 20. FIG. 10 is a diagram 1000 illustrating a transparent liner 1010 on the lumen of the working channel 36. During surgical procedure, accidental laser emission when the laser fiber 22 is inside the working channel 36 may result in laser energy 1001 dispersing out of the sides of the transparent liner 1010, which may cause damage to the inner components of the endoscope 20 such as those adjacent to the transparent liner 1010 and to the distal end of the endoscope 20.

Figure 11:
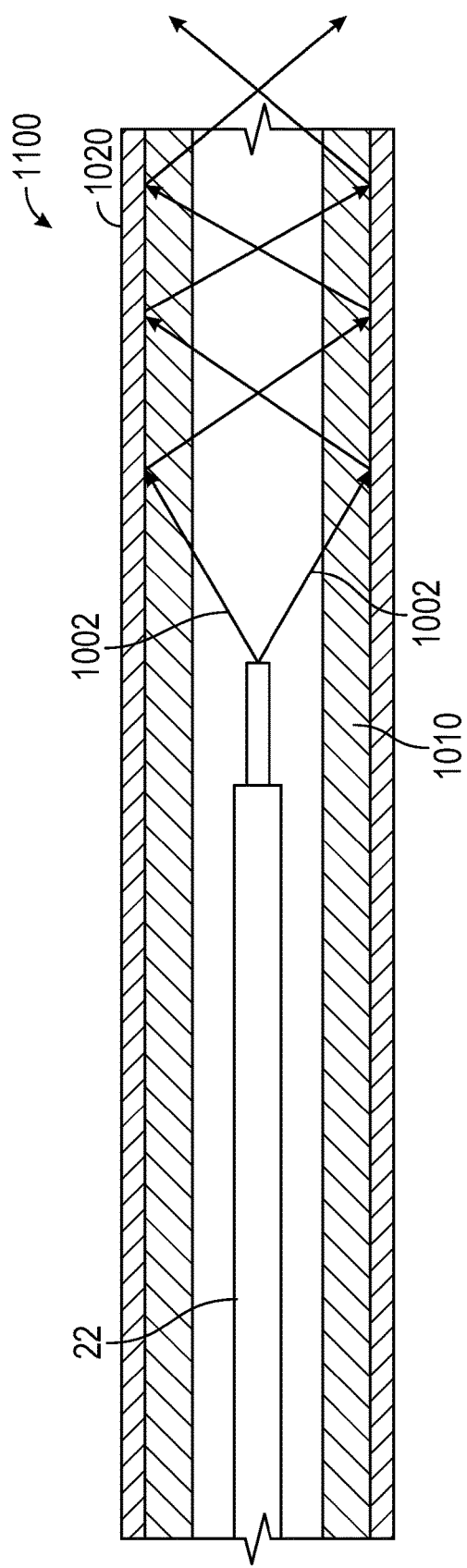
FIG. 11 illustrates an example of an endoscope that includes a reflective coating over a transparent liner of the working channel of an endoscope.

The present document discusses, according to various examples, solutions to prevent or reduce damage due to accidental laser firing from within the working channel 36. FIG. 11 illustrates an example of an endoscope 1100 that includes a reflective coating 1020 over the transparent liner 1010 of the working channel 36. The reflective coating 1020 may comprise reflective material, such as aluminum, silver, gold or copper in the wavelength range of laser emission. In some examples, the reflection surface can include a reflective coating comprised of one or more of Barium Sulfate, Magnesium Oxide, Polytetrafluoroethylene (PTFE), a dielectric high-reflection (HR) coating, a dichroic mirror, or a reflective photonic structure. The reflective coating 1002 may be applied using vacuum metallization/deposition, spray coating, vapor deposition, conductive painting or flame spraying, among other techniques.

As illustrated in FIG. 11, laser energy 1002 emitted from laser fiber 22 when it is inside the working channel 36 may be substantially reflected by the reflective coating 1020. The laser energy 1002 bounces along the walls of the liner 1010, and propagates to and out of the distal end of the working channel 36. As such, the amount of damage to various components of the endoscope caused by laser dispersion can be substantially reduced. An endoscope with the reflective coating on working channel liner as described herein can advantageously minimize accidental damage to the scope during procedures, reduce the procedure and repair costs for reusable scopes, and decrease the amount of time the reusable scopes are out of service. In some examples, the reflective coating can be applied to the liners of a single use scope, thereby minimizing accidental damage which may result in multiple scopes for one procedure.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described below, may be implemented, practiced, or utilized in any combination (for example, any combination that is suitable, practicable, and/or feasible) and are not limited only to those combinations described herein and/or included in the appended claims.

Example 1 is a method of feedback control of a surgical laser system, the method comprising: directing light from a distal end of an endoscope to a target; optically detecting an amount of the light reflected from the target; transmitting the optically detected amount of light through a laser fiber extending through a working channel of the endoscope; determining, based on the optically detected amount of light, a position of a distal end of the laser fiber relative to the distal end of the endoscope; and generating a control signal to the surgical laser system to adjust laser emission through the laser fiber.

In Example 2, the subject matter of Example 1 optionally includes, wherein determining the position of distal end of the laser fiber relative to the distal end of the endoscope includes: if the optically detected amount of light is greater than a predetermined value, determining that the distal end of the laser fiber extends beyond the distal end of the endoscope; and if the optically detected amount of light is less than a predetermined value, determining that the distal end of the laser fiber does not extend beyond the distal end of the endoscope, and generating a control signal to prevent the laser from emitting laser energy through the laser fiber.

In Example 3, the subject matter of Example 2 optionally includes providing to a user a first indicator of the distal end of the laser fiber extending beyond the distal end of the endoscope, and a second indicator of the distal end of the laser fiber not extending beyond the distal end of the endoscope.

In Example 4, the subject matter of any one or more of Examples 1-3 optionally includes, wherein determining the position of distal end of the laser fiber relative to the distal end of the endoscope is based on an increase or a rate of increase of detected amount of light over time.

In Example 5, the subject matter of any one or more of Examples 1-4 optionally includes, wherein generating the control signal to the surgical laser system includes: if the optically detected amount of light is greater than a predetermined value, generating a control signal to allow the surgical laser system to emit laser energy through the laser fiber; and if the optically detected amount of light is less than a predetermined value, generating a control signal to prevent the surgical laser system from emitting laser energy through the laser fiber.

In Example 6, the subject matter of Example 5 optionally includes detecting, using an optical detector, a wavelength of the directed light, wherein the generating the control signal to the surgical laser system to emit laser energy is further based on the detected wavelength of the directed light.

In Example 7, the subject matter of Example 6 optionally includes identifying the target as one of a plurality of target types based on the light reflected from the target using a feedback analyzer; and wherein generating the control signal to the surgical laser system to adjust laser emission is further based on the identification of the target.

In Example 8, the subject matter of Example 7 optionally includes determining one or more spectroscopic properties of the light reflected from the target using a spectroscopy system, and identifying the target based on the one or more spectroscopic properties.

In Example 9, the subject matter of Example 8 optionally includes, wherein determining one or more spectroscopic properties includes using at least one of: a UV-VIS reflection spectroscopy; a fluorescent spectroscopy; a Fourier-Transform infrared spectroscopy; or a Raman spectroscopy.

Example 10 is a laser feedback control system, comprising: an endoscope including an optical detector configured to detect an amount of light reflected from a target in response to illumination of the target from a distal end of the endoscope; a laser fiber extending through a working channel of the endoscope, the laser fiber configured to transmit the detected amount of light reflected from the target; and a controller configured to: determine, based on the optically detected amount of light, a position of a distal end of the laser fiber relative to the distal end of the endoscope; and generate a control signal to a surgical laser system to adjust laser emission through the laser fiber.

In Example 11, the subject matter of Example 10 optionally includes, wherein the controller is configured to determine the position of the distal end of the laser fiber including: if the optically detected amount of light is greater than a predetermined value, determine that the distal end of the laser fiber extends beyond the distal end of the endoscope; and if the optically detected amount of light is less than a predetermined value, determine that the distal end of the laser fiber does not extend beyond the distal end of the endoscope.

In Example 12, the subject matter of any one or more of Examples 10-11 optionally includes a laser interlock coupled to the surgical laser system, the laser interlock configured to, in accordance with the control signal: enable the surgical laser system to emit laser energy through the laser fiber if the optically detected amount of light is greater than a predetermined value; and prevent the surgical laser system from emitting laser energy through the laser fiber if the optically detected amount of light is less than a predetermined value.

In Example 13, the subject matter of any one or more of Examples 10-12 optionally includes: a spectroscopy system configured to determine one or more spectroscopic properties from the light reflected from the target; and a feedback analyzer configured to identify the target as one of a plurality of target types based on the one or more spectroscopic properties; wherein the controller is configured to generate the control signal to the surgical laser system to adjust laser emission further based on the identification of the target.

In Example 14, the subject matter of Example 13 optionally includes, wherein the controller is configured to determine the position of a distal end of the laser fiber relative to the distal end of the endoscope based on an increase or a rate of increase of detected amount of light over time.

Example 15 is an apparatus, comprising: at least one processor; and at least one non-transitory memory including computer program code, the at least one non-transitory memory and the computer program code configured to, with the at least one processor, cause the apparatus at least to perform: directing light from a distal end of an endoscope to a target; optically detecting an amount of the directed light reflected from the target; transmitting the optically detected amount of light through a laser fiber extending through a working channel of the endoscope; determining, based on the optically detected amount of light, a position of a distal end of the laser fiber relative to the distal end of the endoscope; and generating a control signal to a surgical laser system to adjust laser emission through the laser fiber.

In Example 16, the subject matter of Example 15 optionally includes, wherein the at least one non-transitory memory and the computer program code are configured to, with the at least one processor, cause the apparatus to at least perform: if the optically detected amount of light is greater than a predetermined value, determining that the distal end of the laser fiber extends beyond the distal end of the endoscope; and if the optically detected amount of light is less than a predetermined value, determining that the distal end of the laser fiber does not extend beyond the distal end of the endoscope, and generating a control signal to prevent the surgical laser system from emitting laser energy through the laser fiber.

In Example 17, the subject matter of any one or more of Examples 15-16 optionally includes, wherein the at least one non-transitory memory and the computer program code are configured to, with the at least one processor, cause the apparatus to, determine the position of distal end of the laser fiber relative to the distal end of the endoscope based on an increase or a rate of increase of detected amount of light over time.

In Example 18, the subject matter of any one or more of Examples 15-17 optionally includes, wherein the at least one non-transitory memory and the computer program code are configured to, with the at least one processor, cause the apparatus to at least perform: if the optically detected amount of light is greater than a predetermined value, generating a control signal to allow the surgical laser system to emit laser energy through the laser fiber; and if the optically detected amount of light is less than a predetermined value, generating a control signal to prevent the surgical laser system from emitting laser energy through the laser fiber.

In Example 19, the subject matter of Example 18 optionally includes, wherein the at least one non-transitory memory and the computer program code are configured to, with the at least one processor, cause the apparatus to at least perform: identifying the target as one of a plurality of target types based on the light reflected from the target; and generating a control signal to the surgical laser system to adjust laser emission based on the identification of the target.

In Example 20, the subject matter of Example 19 optionally includes, wherein the at least one non-transitory memory and the computer program code are configured to, with the at least one processor, cause the apparatus to at least perform: determining one or more spectroscopic properties of the light reflected from the target; and identifying the target as one of the plurality of target types based on the one or more spectroscopic properties.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of feedback control of a surgical laser system, the method comprising:
    directing light from a distal end of an endoscope to a target;
    optically detecting an amount of the light reflected from the target using an optical detector associated with the endoscope;
    transmitting the optically detected amount of light through a laser fiber extending through a working channel of the endoscope;
    determining, via a controller, based on the optically detected amount of light, a position of a distal end of the laser fiber relative to the distal end of the endoscope; and
    generating, via the controller, a control signal to the surgical laser system to adjust laser emission through the laser fiber.

2. The method of claim 1, wherein determining the position of distal end of the laser fiber relative to the distal end of the endoscope includes:
    if the optically detected amount of light is greater than a predetermined value, determining that the distal end of the laser fiber extends beyond the distal end of the endoscope; and
    if the optically detected amount of light is less than a predetermined value, determining that the distal end of the laser fiber does not extend beyond the distal end of the endoscope, and generating a control signal to prevent the laser from emitting laser energy through the laser fiber.

3. The method of claim 2, further comprising providing to a user a first indicator of the distal end of the laser fiber extending beyond the distal end of the endoscope, and a second indicator of the distal end of the laser fiber not extending beyond the distal end of the endoscope.

4. The method of claim 1, wherein determining the position of distal end of the laser fiber relative to the distal end of the endoscope is based on an increase or a rate of increase of detected amount of light over time.

5. The method of claim 1, wherein generating the control signal to the surgical laser system includes:
    if the optically detected amount of light is greater than a predetermined value, generating a control signal to a laser interlock to allow the surgical laser system to emit laser energy through the laser fiber; and
    if the optically detected amount of light is less than a predetermined value, generating a control signal to the laser interlock to prevent the surgical laser system from emitting laser energy through the laser fiber.

6. The method of claim 5, further comprising detecting, using the optical detector, a wavelength of the directed light, wherein the generating the control signal to the surgical laser system to emit laser energy is further based on the detected wavelength of the directed light.

7. The method of claim 1, further comprising identifying the target as one of a plurality of target types based on the light reflected from the target using a feedback analyzer; and
wherein generating the control signal to the surgical laser system to adjust laser emission is further based on the identification of the target.

8. The method of claim 7, further comprising determining one or more spectroscopic properties of the light reflected from the target using a spectroscopy system, and identifying the target based on the one or more spectroscopic properties.

9. The method of claim 8, wherein determining one or more spectroscopic properties includes using at least one of:
a UV-VIS reflection spectroscopy;
a fluorescent spectroscopy;
a Fourier-Transform infrared spectroscopy; or
a Raman spectroscopy.

10. A laser feedback control system, comprising:
an endoscope and an optical detector configured to detect an amount of light reflected from a target in response to illumination light directed to the target from a distal end of the endoscope;
a laser fiber extending through a working channel of the endoscope, the laser fiber configured to transmit the detected amount of light reflected from the target; and
a controller configured to:
determine, based on the optically detected amount of light, a position of a distal end of the laser fiber relative to the distal end of the endoscope; and
generate a control signal to a surgical laser system to adjust laser emission through the laser fiber.

11. The laser feedback control system of claim 10, wherein the controller is configured to determine the position of the distal end of the laser fiber including:
if the optically detected amount of light is greater than a predetermined value, determine that the distal end of the laser fiber extends beyond the distal end of the endoscope; and
if the optically detected amount of light is less than a predetermined value, determine that the distal end of the laser fiber does not extend beyond the distal end of the endoscope.

12. The laser feedback control system of claim 10, comprising a laser interlock coupled to the surgical laser system, the laser interlock configured to, in accordance with the control signal:
enable the surgical laser system to emit laser energy through the laser fiber if the optically detected amount of light is greater than a predetermined value; and
prevent the surgical laser system from emitting laser energy through the laser fiber if the optically detected amount of light is less than a predetermined value.

13. The laser feedback control system of claim 10, further comprising:
a spectroscopy system configured to determine one or more spectroscopic properties from the light reflected from the target; and
a feedback analyzer configured to identify the target as one of a plurality of target types based on the one or more spectroscopic properties;
wherein the controller is configured to generate the control signal to the surgical laser system to adjust laser emission further based on the identification of the target.

14. The laser feedback control system of claim 13, wherein the controller is configured to determine the position of a distal end of the laser fiber relative to the distal end of the endoscope based on an increase or a rate of increase of detected amount of light over time.

15. The laser feedback control system of claim 13, wherein the spectroscopy system is configured to determine the one or more spectroscopic properties using at least one of:
a UV-VIS reflection spectroscopy;
a fluorescent spectroscopy;
a Fourier-Transform infrared spectroscopy; or
a Raman spectroscopy.

16. The laser feedback control system of claim 10, wherein the controller is configured generate indicators to a user including a first indicator of the distal end of the laser fiber extending beyond the distal end of the endoscope, and a second indicator of the distal end of the laser fiber not extending beyond the distal end of the endoscope.

17. The laser feedback control system of claim 10, wherein the optical detector is configured to detect a wavelength of the illumination light, wherein to generate the control signal to the surgical laser system to adjust the laser emission is further based on the detected wavelength of the illumination light.

18. An apparatus, comprising:
at least one processor; and
at least one non-transitory memory including computer program code, the at least one non-transitory memory and the computer program code configured to, with the at least one processor, cause the apparatus at least to perform:
directing light from a distal end of an endoscope to a target;
optically detecting an amount of the directed light reflected from the target;
transmitting the optically detected amount of light through a laser fiber extending through a working channel of the endoscope;
determining, based on the optically detected amount of light, a position of a distal end of the laser fiber relative to the distal end of the endoscope; and
generating a control signal to a surgical laser system to adjust laser emission through the laser fiber.

19. The apparatus of claim 18, wherein the at least one non-transitory memory and the computer program code are configured to, with the at least one processor, cause the apparatus to at least perform:
if the optically detected amount of light is greater than a predetermined value, determining that the distal end of the laser fiber extends beyond the distal end of the endoscope; and
if the optically detected amount of light is less than a predetermined value, determining that the distal end of the laser fiber does not extend beyond the distal end of the endoscope, and generating a control signal to prevent the surgical laser system from emitting laser energy through the laser fiber.

20. The apparatus of claim 18, wherein the at least one non-transitory memory and the computer program code are configured to, with the at least one processor, cause the apparatus to, determine the position of distal end of the laser fiber relative to the distal end of the endoscope based on an increase or a rate of increase of detected amount of light over time.

21. The apparatus of claim 18, wherein the at least one non-transitory memory and the computer program code are configured to, with the at least one processor, cause the apparatus to at least perform:

if the optically detected amount of light is greater than a predetermined value, generating a control signal to allow the surgical laser system to emit laser energy through the laser fiber; and if the optically detected amount of light is less than a predetermined value, generating a control signal to prevent the surgical laser system from emitting laser energy through the laser fiber.

22. The apparatus of claim 21, wherein the at least one non-transitory memory and the computer program code are configured to, with the at least one processor, cause the apparatus to at least perform:

identifying the target as one of a plurality of target types based on the light reflected from the target; and generating a control signal to the surgical laser system to adjust laser emission based on the identification of the target.

23. The apparatus of claim 22, wherein the at least one non-transitory memory and the computer program code are configured to, with the at least one processor, cause the apparatus to at least perform:

determining one or more spectroscopic properties of the light reflected from the target; and identifying the target as one of the plurality of target types based on the one or more spectroscopic properties.

* * * * *